United States Patent
Choe et al.

(10) Patent No.: US 10,067,215 B2
(45) Date of Patent: Sep. 4, 2018

(54) PHANTOM FOR EVALUATING PERFORMANCE OF MAGNETIC RESONANCE IMAGING APPARATUS USING ULTRA HIGH FIELD

(71) Applicant: THE CATHOLIC UNIVERSITY OF KOREA INDUSTRY—ACADEMIC COOPERATION FOUNDATION, Seoul (KR)

(72) Inventors: Bo Young Choe, Seoul (KR); Kyu-Ho Song, Gyeonggi-do (KR); Do-Wan Lee, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 649 days.

(21) Appl. No.: 14/685,787

(22) Filed: Apr. 14, 2015

(65) Prior Publication Data
US 2016/0282439 A1    Sep. 29, 2016

(30) Foreign Application Priority Data
Mar. 25, 2015  (KR) .................. 10-2015-0041535

(51) Int. Cl.
*G01V 3/00*    (2006.01)
*G01R 33/58*   (2006.01)
*G01R 33/20*   (2006.01)
*G01N 24/00*   (2006.01)
*A61B 5/055*   (2006.01)

(52) U.S. Cl.
CPC ............. *G01R 33/58* (2013.01); *G01N 24/00* (2013.01); *G01R 33/20* (2013.01); *A61B 5/055* (2013.01)

(58) Field of Classification Search
CPC ........ G01R 33/58; G01R 33/20; G01N 24/00; A61B 5/055
USPC ................................. 324/307, 318
See application file for complete search history.

(56) References Cited

U.S. PATENT DOCUMENTS

| | | | | |
|---|---|---|---|---|
| 4,644,276 A | * | 2/1987 | Sierocuk | G01R 33/58 324/300 |
| 5,036,280 A | * | 7/1991 | Chesavage | G01R 33/58 324/308 |

* cited by examiner

*Primary Examiner* — Amy He
(74) *Attorney, Agent, or Firm* — Eric W. Cernyar; James W. Huffman

(57) ABSTRACT

A new multi-purpose phantom evaluates the performance of an ultra high field Magnetic Resonance Imaging (MRI) apparatus. The phantom can assess a degree of diagnostic capability of an MRI apparatus using imaging conditions and variables and simultaneously analyze and evaluate performance of Magnetic Resonance Imaging (MRI), performance of Magnetic Resonance Spectroscopy (MRS) and metabolic components of a human body within a predetermined range of error and limit.

21 Claims, 11 Drawing Sheets

PHANTOM FOR EVALUATING PERFORMANCE OF MAGNETIC RESONANCE IMAGING APPARATUS USING ULTRA HIGH FIELD

BACKGROUND OF THE INVENTION

Field of the Invention

The present invention relates to a phantom for evaluating performance of an ultra high field Magnetic Resonance Imaging (MRI) apparatus. Specifically, the present invention relates to a multi-purpose phantom which can grasp a degree of diagnostic capability of an MRI apparatus using a comprehensive result of imaging conditions and variables and simultaneously analyze and evaluate performance of Magnetic Resonance Imaging (MRI), performance of Magnetic Resonance Spectroscopy (MRS) and metabolic components of a human body within a predetermined range of error and limit.

Background of the Related Art

Magnetic Resonance Imaging (MRI) is a representative imaging technique capable of measuring brain functions of a human body, and Magnetic Resonance Spectroscopy (MRS) which can detect chemical compositions of brain tissues by providing structural images giving a variety of image contrasts is diversely used.

The Magnetic Resonance Imaging (MRI) uses a nuclear magnetic resonance principle as one of imaging techniques. That is, if a human body is put into a Magnetic Resonance Imaging (MRI) apparatus generating a magnetic field and a high frequency is generated, hydrogen nuclei of the human body resonate, and a magnetic resonance image can be created by measuring difference of signals generated at this point and reconfiguring and imaging a result of the measurement through a computer.

The magnetic resonance imaging is featured by harmlessness to a human body unlike X-ray Computer Tomography (CT) which is harmful to the human body by using X-ray, and the MRI has an advantage of being free from direction while the main idea of the CT is cross-sectional images.

Generally, a human ACR phantom (American college of radiology-magnetic resonance imaging phantom) and a human AAPM phantom (American association of physicists in medicine) are used to evaluate performance of an MRI apparatus.

That is, performance of human MRI is evaluated based on a standard protocol for a precise and accurate analysis and evaluation of image interpretation and clinical equipment.

A phantom used for evaluating performance of a human MRI apparatus is used to predict existence of abnormality (error), present the portions containing an error focusing on diagnosis and access and solve the error when an event going out of a permitted error range and a limited error range of the human MRI apparatus occurs.

The phantom confirms whether or not hardware of the human MRI apparatus and related MRI systems normally operate, and when an error going out of the permitted error range occurs, it checks and reviews related elements and accesses the elements to solve the problem of diagnostic error through daily, weekly and monthly quality control.

In a research institute, a company or a school aiming at studies and experiments on a field uncovered in the human diagnostic area, MRI apparatuses for studying small animals, as well as the human MRI apparatuses, are used in many fields.

Therefore, accurate quality control in the diagnostic area is acutely needed for MRI apparatuses for studying small animals, as well as human MRI apparatuses.

In relation to performance evaluation of an MRI apparatus for studying small animals, the Magnetic Resonance Imaging and the Magnetic Resonance Spectroscopy are methods performing chemical verification and quantization of brain metabolites or liver metabolites of a small animal, and a method of providing metabolite information of a body based on anatomical and histological images is applied.

In addition, the Magnetic Resonance Spectroscopy used for evaluation of an animal MRI apparatus is used for discovery of early diagnosis, together with changes of metabolites in a cell, a tissue or an organ based on analysis of an acquired spectrum.

That is, the Magnetic Resonance Spectroscopy is a method of distinguishing difference in concentration of diverse metabolites of a human body, which evaluates influence of treatment when a disease is treated, and it may be regarded as a technique capable of performing a quantified chemical analysis on metabolites of the brain and the liver using a technique of early diagnosis accuracy based on a position occurring a disease and changes in the metabolites of the brain and the liver for the purpose of study.

When the Magnetic Resonance Imaging and the Magnetic Resonance Spectroscopy which can be used in an animal MRI apparatus are performed, it needs to evaluate performance of the MRI system in advance.

In relation to this, although an MRS phantom has been developed as shown in Korean Patent Registration No. 10-0961892, which is a document of a prior technique published before the application of the present invention, there is a problem of low temporal efficiency, which is important in the area of diagnosis, and a problem of limiting its method and apparatus to a human MRI apparatus.

Accordingly, development of a micro phantom for executing performance evaluation on an animal MRI apparatus and pursuing optimum temporal efficiency, which is a focal point in the diagnostic area, is very strongly required.

SUMMARY OF THE INVENTION

Therefore, the present invention has been made in view of the above problems, and it is an object of the present invention to provide a phantom for evaluating performance of an ultra high field MRI apparatus. Specifically, an object of the present invention is to provide a user with a multi-purpose phantom which can grasp a degree of diagnostic capability of an MRI apparatus using a comprehensive result of imaging conditions and variables and simultaneously analyze and evaluate performance of Magnetic Resonance Imaging (MRI), performance of Magnetic Resonance Spectroscopy (MRS) and metabolic components of a human body within a predetermined range of error and limit.

The technical problems to be solved in the present invention are not limited to the technical problems mentioned above, and unmentioned other technical problems may be clearly understood by those skilled in the art from the following descriptions.

To accomplish the above object, according to one aspect of the present invention, there is provided a phantom for evaluating performance of an ultra high field Magnetic Resonance Imaging (MRI) apparatus, the phantom including: an outer container opened and closed using a stopper and formed with an insertion hole for injecting components of a liver metabolite and a lipid; an inner container for quantitatively evaluating the components of the liver metabolite and the lipid, acquiring an MRI image using a spin echo sequence, and acquiring a relaxation time through spectroscopy using a single voxel technique of the MRI apparatus; a geometric accuracy evaluation apparatus installed at an upper end portion of the outer container in a shape of three-dimensional lattice type frame; slice position evaluation apparatuses of different shapes, capable of measuring a position of a slice in a middle of the outer container; a contrast resolution evaluation apparatus configured of a plurality of holes in the middle of the outer container to perform evaluation at regular intervals; a spatial resolution evaluation apparatus installed inside the outer container, in which a plurality of hole bundles configured of space evaluation holes is formed to have a same diameter and arranged in an evaluation frame in parallel at regular intervals to have holes of different diameters in each of the hole bundles; a slice thickness evaluation apparatus installed at a height a same as that of the spatial resolution evaluation apparatus and attached to the outer container to be formed in a shape of a stair; and a brain metabolite evaluation apparatus configured of a plurality of layers at a lower portion of the outer container.

In addition, the phantom for evaluating performance of an ultra high field Magnetic Resonance Imaging (MRI) apparatus may be used for small animals.

In addition, the outer container may further include an injection hole, in which holes uniformly distributed from a center portion of a top surface are opened and closed using a plurality of stoppers, and the insertion hole may be formed in a shape of an arc spaced apart from the injection hole by a predetermined distance.

In addition, the inner container may acquire T1 and T2 relaxation images by using a spin echo sequence of a method of acquiring a main image of the MRI image, acquire T1 and T2 relaxation images related to the inner container through spectroscopy using the single voxel technique of the MRI apparatus, and compare the acquired T1 and T2 relaxation images and the acquired T1 and T2 relaxation spectra with each other.

In addition, the slice position evaluation apparatus may measure four step slice positions of a cross shape in the middle of the outer container.

In addition, the plurality of holes of the contrast resolution evaluation apparatus may be formed in a circular shape and arranged regularly.

In addition, the plurality of layers of the brain metabolite evaluation apparatus may be configured of four layers.

In addition, the inner container may include: a stopper formed of a polyethylene bolt capable of simultaneously injecting air and preventing leakage of water through a plurality of holes; and a rubber ring inserted around a lower end portion of the stopper.

In addition, a solution mimicking the liver metabolite may be injected into the inner container, and a quantitative evaluation and analysis may be performed by changing a type and concentration of the solution.

In addition, a solution mimicking the lipid may be injected into the inner container, and a quantitative evaluation and analysis may be performed by changing amounts of components constituting the solution.

In addition, each lattice frame of the shape of three-dimensional lattice type frame may be regularly configured of same lattices and used for analysis on x, y and z axes.

In addition, a pillar frame functioning as a supporting body of the geometric accuracy evaluation apparatus may be additionally inserted.

In addition, the slice position evaluation apparatus may be configured of three layers, and height of the three layers may decrease at regular intervals counterclockwise.

In addition, the space evaluation holes of a regular array formed on each disk of the contrast resolution evaluation apparatus may be arranged in bundles at three positions on the disk.

In addition, the hole bundles of the spatial resolution evaluation apparatus may be formed by arranging a plurality of space evaluation holes of a same diameter at a predetermined position and grouping the space evaluation holes in a diamond shape.

In addition, the slice thickness evaluation apparatus may be a structure of a same width, formed in a shape obliquely sloping down toward left and right.

In addition, a spatial resolution evaluation and a slice thickness evaluation may be simultaneously performed using one slice since the spatial resolution evaluation apparatus and the slice thickness evaluation apparatus are arranged in a row.

In addition, the inner container may be configured of layers of rectangular parallelepiped steps having inner diameters gradually increasing from a top to a bottom.

In addition, a solution mimicking a brain metabolite may be injected into the stepped layers from an upper end portion of the inner container.

In addition, a copper sulfate solution and a sodium chloride aqueous solution may be injected into the inner container through two injection holes formed on a bottom.

In addition, the outer container, the inner container, the geometric accuracy evaluation apparatus, the slice position evaluation apparatus, the contrast resolution evaluation apparatus, the spatial resolution evaluation apparatus, the slice thickness evaluation apparatus and the brain metabolite evaluation apparatus may be configured of an acrylic material.

DETAILED DESCRIPTION OF THE PREFERRED EMBODIMENT

Magnetic Resonance Imaging (MRI) is a representative imaging technique capable of measuring brain function of a human body, and Magnetic Resonance Spectroscopy (MRS) capable of detecting chemical compositions of a brain tissue by providing structural images giving diverse image contrasts is diversely used.

Although a Cone-Type 8*8 CSI Phantom has been invented in the past to be suitable for Multi-Voxel Spectroscopy (MVS) as a Chemical Shift Imaging (CSI) phantom, the internal structure of the conventional cone-type phantom is complex since the emphasis is put on the MVS.

Such a complex internal structure has a limit in obtaining a high quality image since it has an influence on shimming of a magnetic field at the time of MRS.

In addition, an inner container of the cone-type phantom has a problem of inducing a Partial Volume Effect (PVE) of inevitably changing image intensity of an area where a voxel is positioned when the voxel is selected.

Particularly, since the conventional cone-type 8*8 CSI phantom cannot obtain a spectrum at all from the phantom when a shimming state of the magnetic field of each apparatus is poor, its utility is not great.

Accordingly, Korean Patent Registration No. 10-0961892 proposes a phantom for evaluating performance of MRS, which can avoid disadvantages of the conventional cone-type phantom by focusing on Single Voxel Spectroscopy (SVS) rather than Multi-Voxel Spectroscopy (MVS) to make inside thereof further concise and forming an inner container in a double-cone shape or a layered dumbbell shape.

Figure 1:
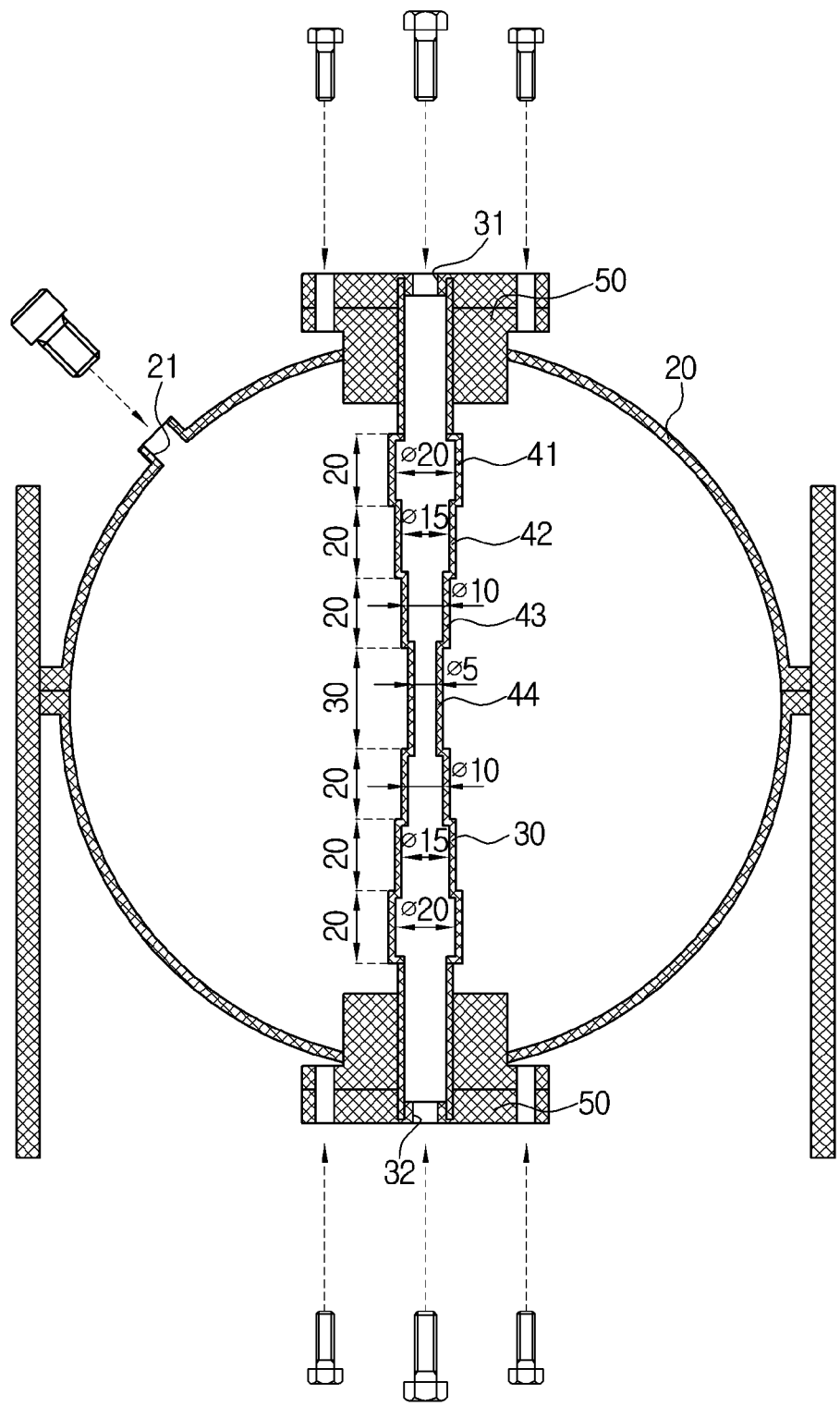
FIG. 1 is a cross-sectional view showing a specific example of a phantom used in the prior art.

Specifically, FIG. 1 is a cross-sectional view showing a phantom according to Korean Patent Registration No. 10-0961892.

Referring to FIG. 1, the conventional phantom for evaluating performance of MRS may include an outer container 20 substantially formed in a sphere shape and an inner container 30 arranged at the center inside the outer container 20, extended in the length direction, and formed in a double-cone shape or a layered dumbbell shape.

Here, the outer container 20 is manufactured to be similar to the head of a human body having a diameter of approximately 20 cm, and at least one insertion hole 21 is formed at one side thereof to inject a material inside the outer container 20.

In addition, the material of the outer container is preferably an acrylic material which is not magnetized even in a strong magnetic field.

The inner container 30 is arranged to have both ends pass through the outer container 20 to be exposed outside. It is preferable that entrance holes 31 and 32 communicating with inside of the inner container 30 are formed at both ends of the inner container 30 to easily remove flowed-in air when the air flows into the inner container 30.

The inner container 30 may be firmly combined with the outer container 20 through a certain connection member 50.

Also, the inner container 30 is preferably configured of an acrylic material which is not magnetized in a strong magnetic field.

The inner container 30 is formed in a tube shape having a plurality of layers of different inner diameters. Since the plurality of layers of the inner container 30 like this may function as a guide in selecting a Volume of Interest (VOI) in which voxels are set, a PVE can be prevented by selecting an accurate VOI, and position accuracy of the VOI can be accurately measured when performance of the MRI apparatus is evaluated.

In an embodiment of the invention according to Korean Patent Registration No. 10-0961892, a phantom having an inner container 30, in which a plurality of layers 41, 42, 43 and 44 is formed to have an inner diameter decreasing sequentially toward the center from both ends, is presented. However, the inner container 30 is not limited to the shape presented in this embodiment, and a variety of shapes, such as a shape having a different number of layers, a shape having inner diameters of the plurality of layers increasing sequentially toward the center from both ends of the inner container 30, and a shape having a plurality of layers of different diameters repetitively positioned one after another, can be applied.

On the other hand, when the inner container 30 of the phantom is formed in a double-cone shape or a layered dumbbell shape having an inner diameter of the center smaller than those of both ends, air bubbles flowed into the inner container 30 may easily move toward the entrance holes 31 and 32 opened toward both ends of the inner container 30, and thus it may be said that the inner container 30 of a double-cone shape or a layered dumbbell shape is advantageous in removing the air bubbles flowed into the inner container 30, compared with an inner container of a different shape.

Total length of the inner container 30 is approximately 15 cm, and height (width) of the pairs of first layers 41, second layers 42 and third layers 43 positioned in order of adjacency to both ends of the inner container 30 is approximately 20 cm respectively, and the height (width) of the fourth layer 44 positioned between the pair of the third layers 43 is approximately 30 cm.

In addition, it is configured such that the inner diameter of the first layer 41 is 20 mm, the inner diameter of the second layer 42 is 15 mm, the inner diameter of the third layer 43 is 10 mm, and the inner diameter of the fourth layer 44 is 5 mm. The fourth layer 44 is positioned at the center of the inner container 30, and the first layers 41, the second layers 42 and the third layers 43 are formed in a symmetrical form with respect to the center. Accordingly, the overall shape of the inner container 30 of the phantom according to the invention disclosed in Korean Patent Registration No. 10-0961892 is formed in a double-cone shape or a layered dumbbell shape.

A copper sulfate solution (CuSO4)(0.7 g/L) is injected inside the outer container 20, i.e., between the outer container and the inner container 30, and the copper sulfate (CuSO4) performs a function of reducing T1 relaxation time of water to increase intensity of an image signal when MRI or MRS is performed.

According to the phantom of FIG. 1 described above, since the amount of metabolite contained in a voxel can be adjusted by configuring the phantom for evaluating performance of MRS to include an inner container arranged inside the outer container to be formed with a plurality of layers of different inner diameters, there is provided an effect of measuring quantity accuracy of a VOI according to the amount of metabolite by showing a big spectrum signal when there is a large amount of metabolite inside the voxel and showing a small spectrum signal when there is a small amount of metabolite inside the voxel although the same voxel is set and an effect of accurately measuring position accuracy of the VOI when performance of the MRI apparatus is measured since the plurality of layers of the inner container of a double-cone shape or a layered dumbbell shape may function as a guide in selecting a Volume of Interest (VOI) in which the voxel is set.

However, companies or schools use animal MRI apparatuses, as well as human MRI apparatuses, in many fields recently. Therefore, accurate quality control in the diagnostic area is earnestly needed for the animal MRI apparatuses, as well as the human MRI apparatuses.

In relation to performance evaluation of the animal MRI apparatuses, the Magnetic Resonance Imaging and the Magnetic Resonance Spectroscopy are methods which perform chemical verification and quantization of brain metabolites or liver metabolites of a small animal, and a method of providing metabolite information of a body based on an anatomical and histological image is applied. In addition, the Magnetic Resonance Spectroscopy used for evaluation of an animal MRI apparatus is used for discovery of early diagnosis, together with changes of metabolites in a cell, a tissue or an organ, based on analysis of an acquired spectrum.

When the Magnetic Resonance Imaging and the Magnetic Resonance Spectroscopy which can be used in an animal MRI apparatus are performed, it needs to evaluate performance of the MRI system in advance.

In relation to this, although it may be considered to apply an MRS phantom described above using FIG. 1, there is a problem in that evaluation on the performance of MRI and MRS, which is important in the diagnosis area, cannot be performed simultaneously and the phantom is limited to a human MRI apparatus.

Accordingly, development of a micro phantom for executing performance evaluation on an animal MRI apparatus and pursuing optimum temporal efficiency, which is the focal point in the diagnostic area, is very strongly required.

As a result, it is desired to propose a phantom for evaluating performance of the animal MRI apparatus described above in this specification, and the invention proposed in this specification can be used as a multi-purpose phantom which can grasp a degree of diagnostic capability of the MRI apparatus using a comprehensive result of imaging conditions and variables and simultaneously analyze and evaluate performance of MRI, performance of MRS and metabolic components of a human body within a predetermined range of error and limit.

Hereinafter, a multi-purpose phantom 100 proposed in the present invention will be described in detail with reference to the accompanying drawings.

Hereinafter, it is assumed for the convenience of explanation that the multi-purpose phantom 100 proposed in the present invention is for small animals and uses an ultra-high field. However, it is apparent that contents of the present invention are not limited to this and may be applied as a modified form.

Hereinafter, the preferred embodiments of the multi-purpose phantom 100 for evaluating performance of an ultra high field animal MRI apparatus according to the present invention will be described in detail with reference to the accompanying drawings.

The present invention is not limited to the embodiments disclosed below and may be implemented in a variety of forms different from each other, and this embodiment is provided only to complete the disclosure of the present invention and to completely inform those skilled in the art of the scope of the present invention.

The multi-purpose phantom 100 for evaluating performance of an ultra high field animal MRI apparatus of the present invention is designed and manufactured to simultaneously acquire performance evaluation of MRI, MRS and functional MRI through one phantom 100 by using an animal MRI apparatus (4.7 T, 9.4 T or higher).

Although manufacturing companies of the existing animal MRI apparatuses provide a phantom 100 capable of performing basic quality control of MRI, the present invention designs and manufactures a phantom 100 capable of performing regular and intensified quality control, rather than a basic quality control, by setting a plurality of steps exceeding the limit of basic performance evaluation.

The multi-purpose phantom 100 for evaluating performance of an ultra high field animal MRI apparatus of the present invention is configured as an apparatus for measuring internal MRI evaluation factors and uses an inner container 120 formed as layers of rectangular parallelepiped steps for performance evaluation of MRS.

The multi-purpose phantom 100 for evaluating performance of an ultra high field animal MRI apparatus of the present invention is a fusion phantom 100, which is a phantom 100 capable of quantitatively performing performance evaluation on an MRI system, and the phantom 100 of the present invention can be used to perform performance evaluation and quality control by developing components of an existing small animal phantom 100 and an MRS phantom 100 by using optimized analysis methods which can simultaneously measure a spatial resolution, a contrast resolution, a slice thickness, a slice position and the like.

Invention of the phantom 100 capable of simultaneously acquiring performance evaluation of MRI, MRS and functional MRI and analyzing metabolites and components of a tissue may be helpful in the field of research and clinical diagnosis of biological, functional, anatomical and metabolic evaluation.

Figure 2:
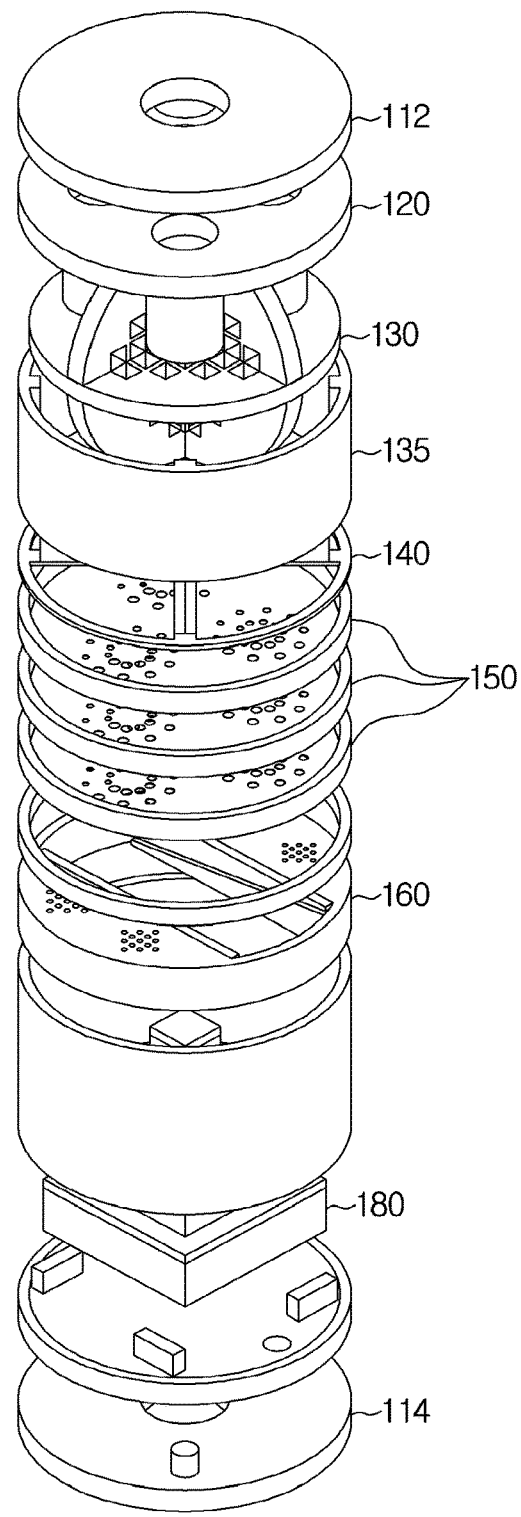
FIG. 2 is a perspective view showing an internal view of an ultra high field multi-purpose performance evaluation phantom related to the present invention, from the top to the bottom.

FIG. 2 is a perspective view showing an internal view of an ultra high field multi-purpose performance evaluation phantom 100 for small animals related to the present invention, from the top to the bottom.

Figure 3:
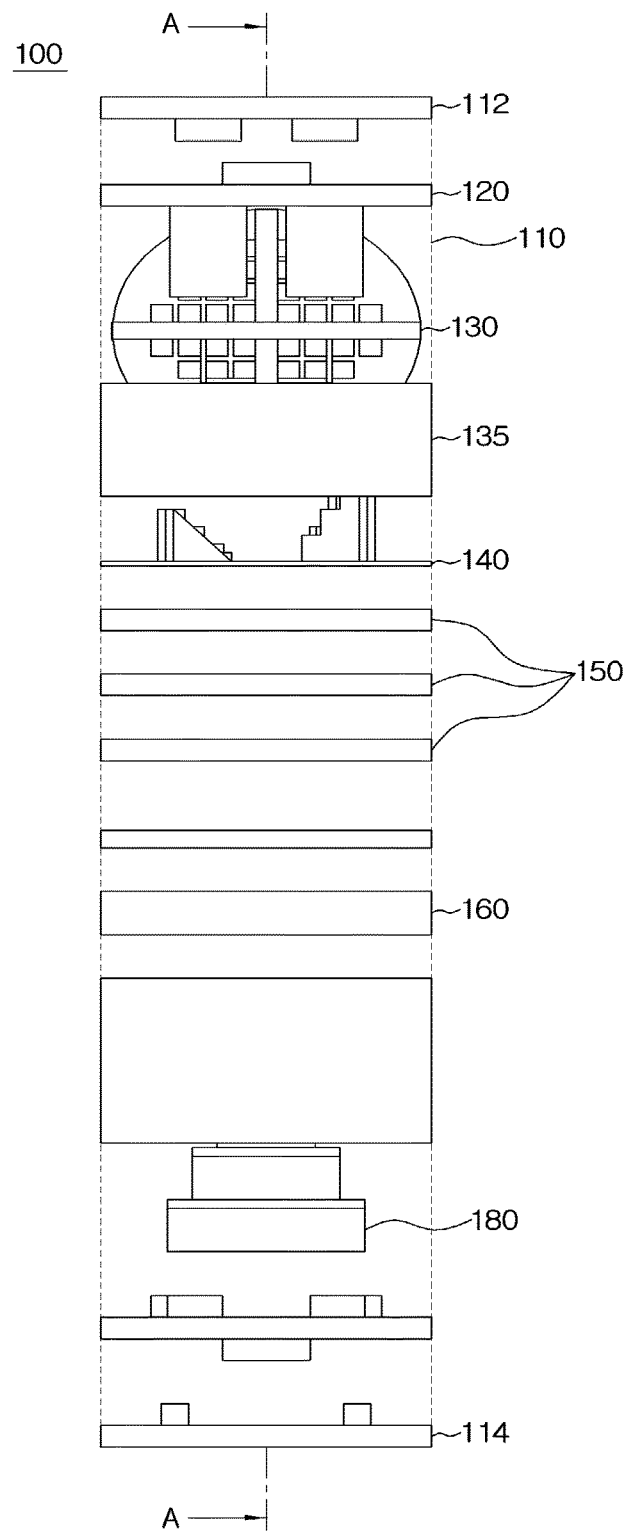
FIG. 3 is a rear view showing an example of a right side surface of an ultra high field multi-purpose performance evaluation phantom related to the present invention.

In addition, FIG. 3 is a rear view showing an example of a right side surface of an ultra high field multi-purpose performance evaluation phantom 100 for small animals related to the present invention.

Figure 4:
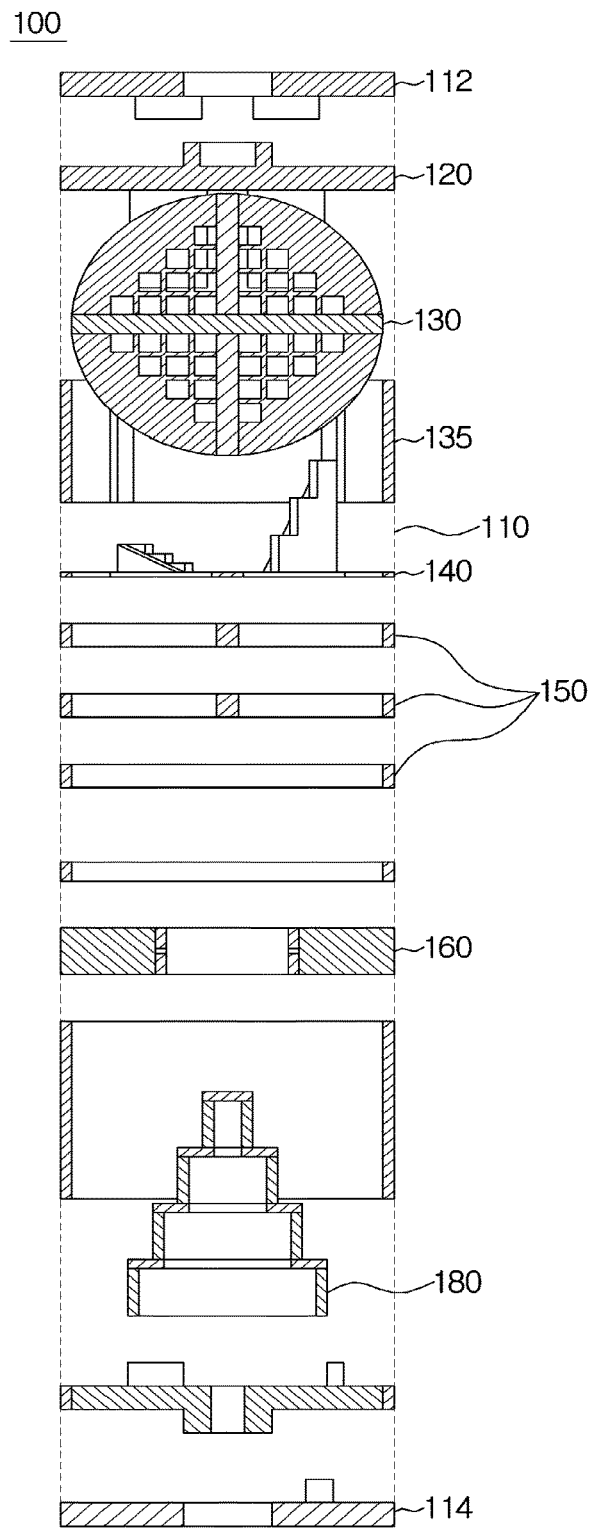
FIG. 4 is a longitudinal sectional view showing a specific example of an ultra high field multi-purpose performance evaluation phantom according to the present invention.

In addition, FIG. 4 is a longitudinal sectional view showing a specific example of an ultra high field multi-purpose performance evaluation phantom 100 for small animals according to the present invention.

Figure 5:
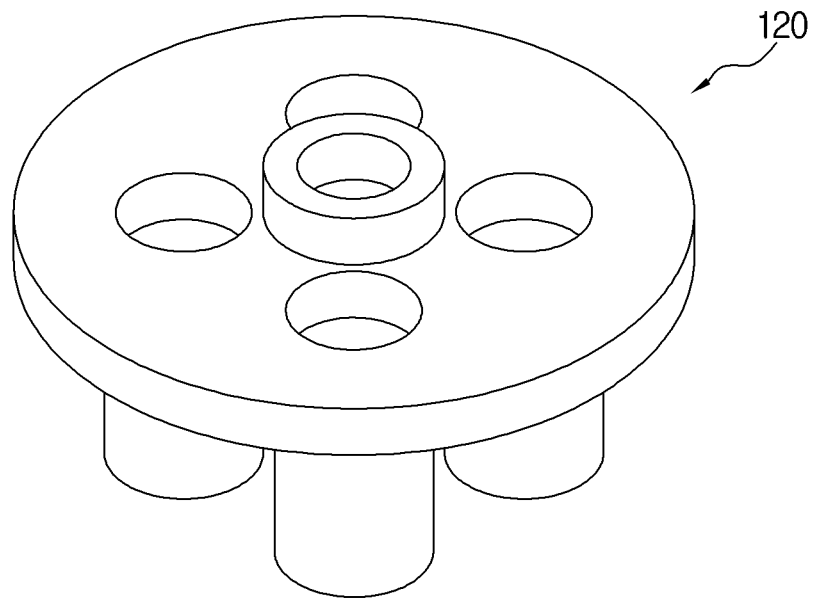
FIG. 5 is a flat sectional view showing an inner container for evaluating components of liver metabolites and lipids of an ultra high field multi-purpose performance evaluation phantom according to the present invention.
Figure 5:
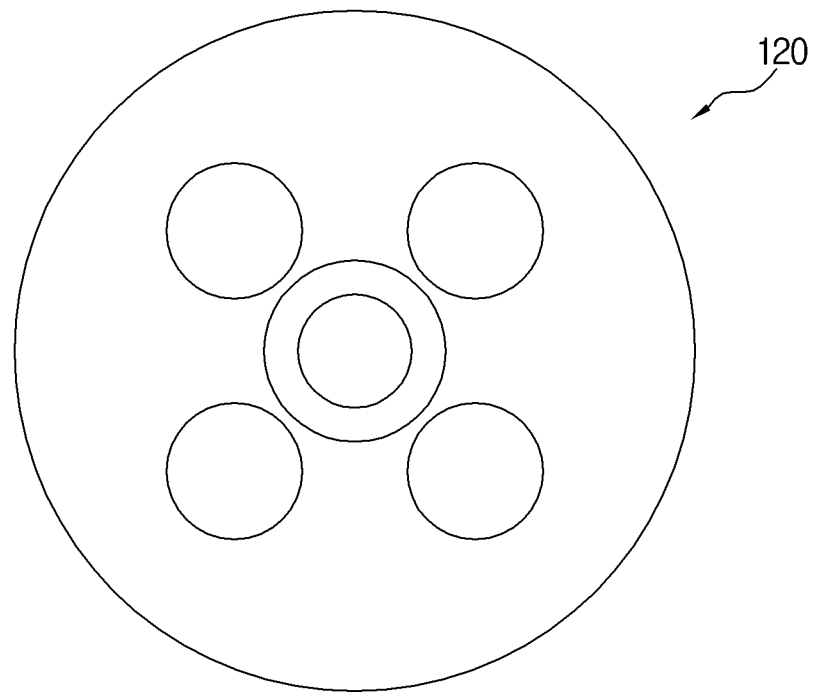

In addition, FIG. 5 is a flat sectional view showing an inner container 120 for evaluating components of liver metabolites and lipids of an ultra high field multi-purpose performance evaluation phantom 100 for small animals according to the present invention.

Figure 6:
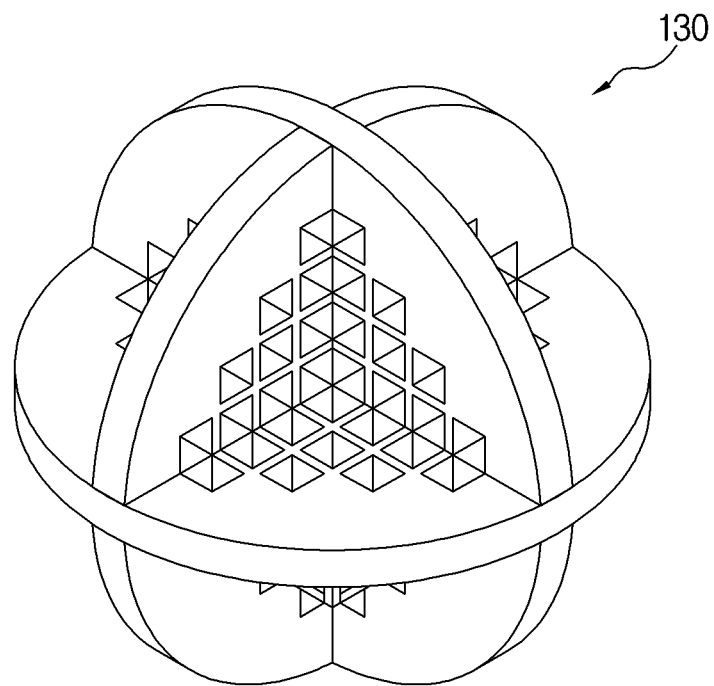
FIG. 6 is a perspective view and a flat sectional view showing a three-dimensional geometric evaluation apparatus of an ultra high field multi-purpose performance evaluation phantom according to the present invention.
Figure 6:
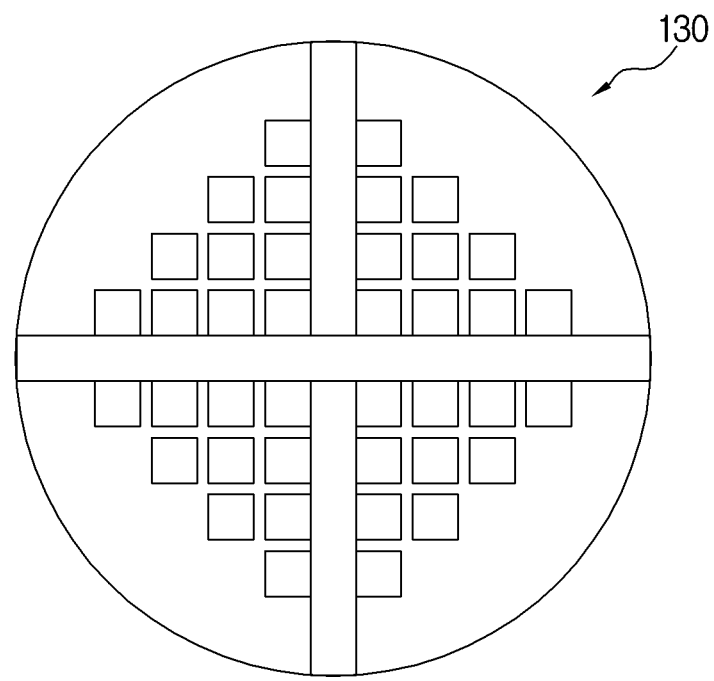

In addition, FIG. 6 is a perspective view and a flat sectional view showing a three-dimensional geometric evaluation apparatus of an ultra high field multi-purpose performance evaluation phantom 100 for small animals according to the present invention.

Figure 7:
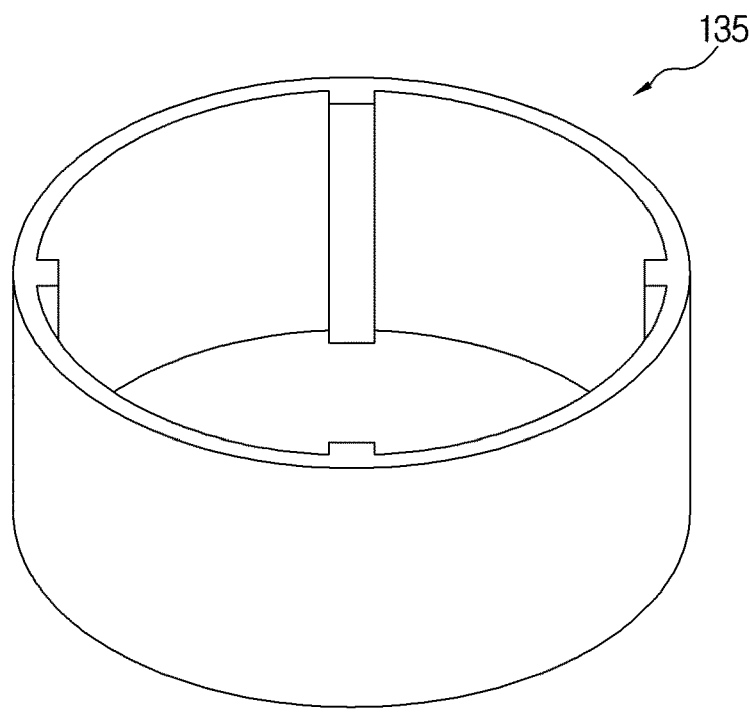
FIG. 7 is a perspective view and a flat sectional view showing a supporting body capable of supporting a three-dimensional geometric evaluation apparatus of an ultra high field multi-purpose performance evaluation phantom according to the present invention.
Figure 7:
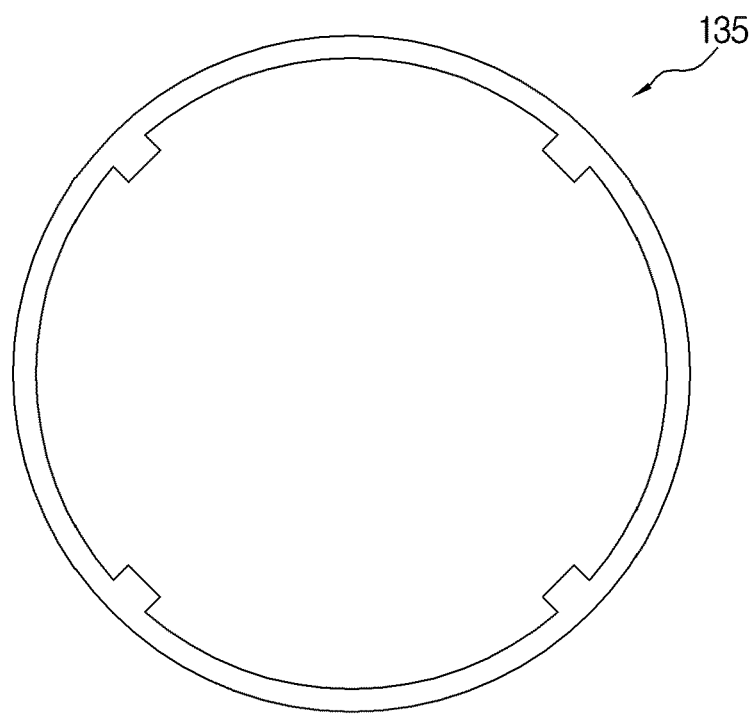

In addition, FIG. 7 is a perspective view and a flat sectional view showing a supporting body capable of supporting a three-dimensional geometric evaluation apparatus of an ultra high field multi-purpose performance evaluation phantom 100 for small animals according to the present invention.

Figure 8:
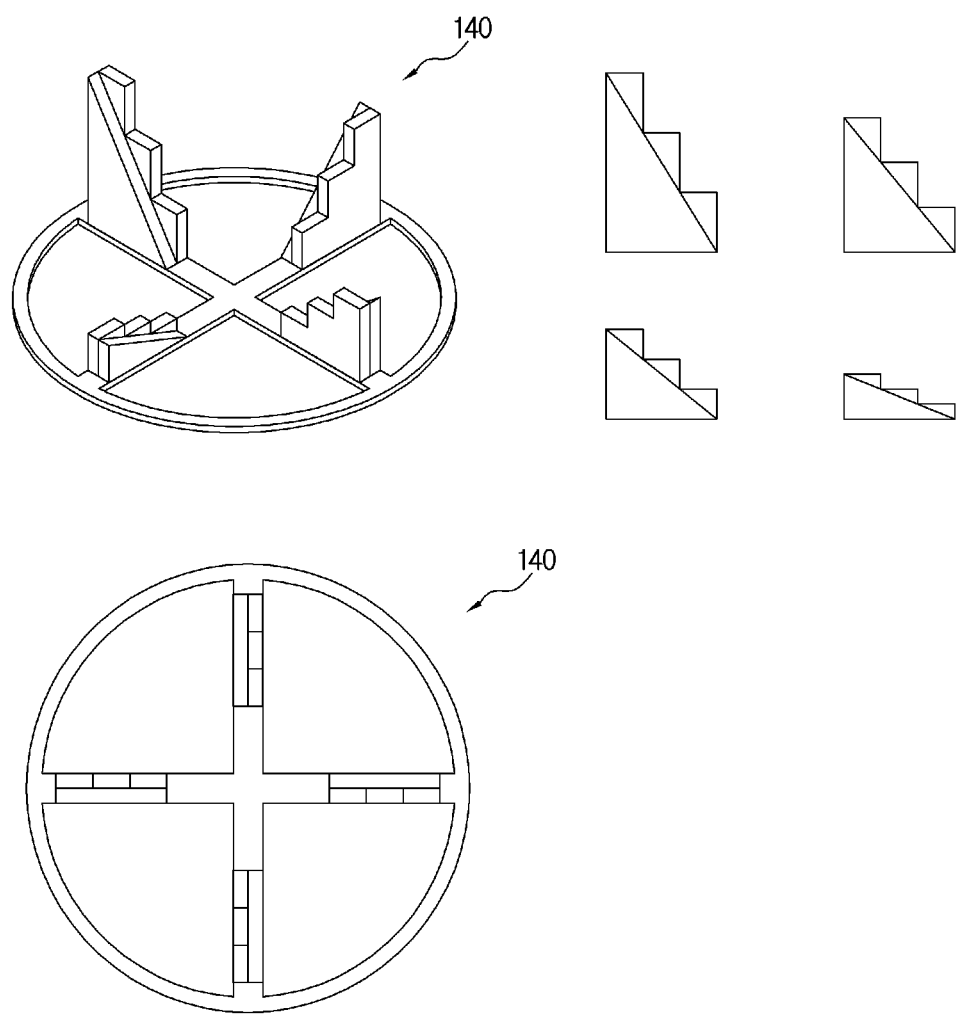
FIG. 8 is a perspective view and a flat sectional view showing a slice position evaluation apparatus of an ultra high field multi-purpose performance evaluation phantom according to the present invention and a longitudinal sectional view showing components thereof.

In addition, FIG. 8 is a perspective view and a flat sectional view showing a slice position evaluation apparatus of an ultra high field multi-purpose performance evaluation phantom 100 for small animals according to the present invention and a longitudinal sectional view showing components thereof.

Figure 9:
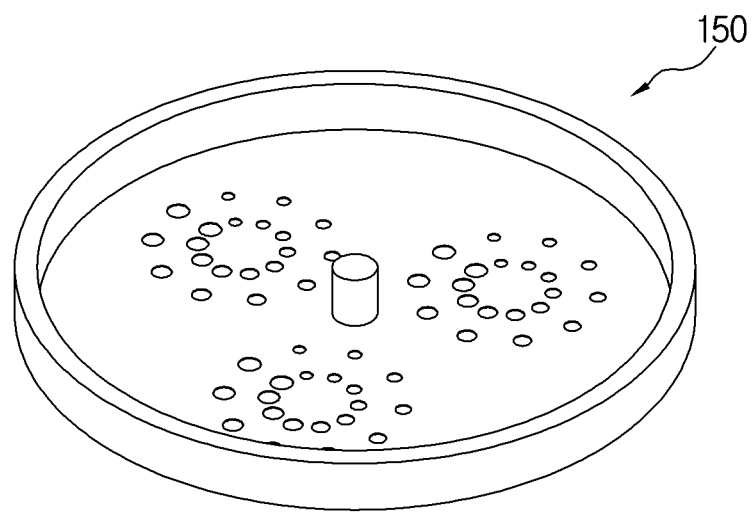
FIG. 9 is a perspective view and a flat sectional view showing a contrast resolution evaluation apparatus of an ultra high field multi-purpose performance evaluation phantom according to the present invention.
Figure 9:
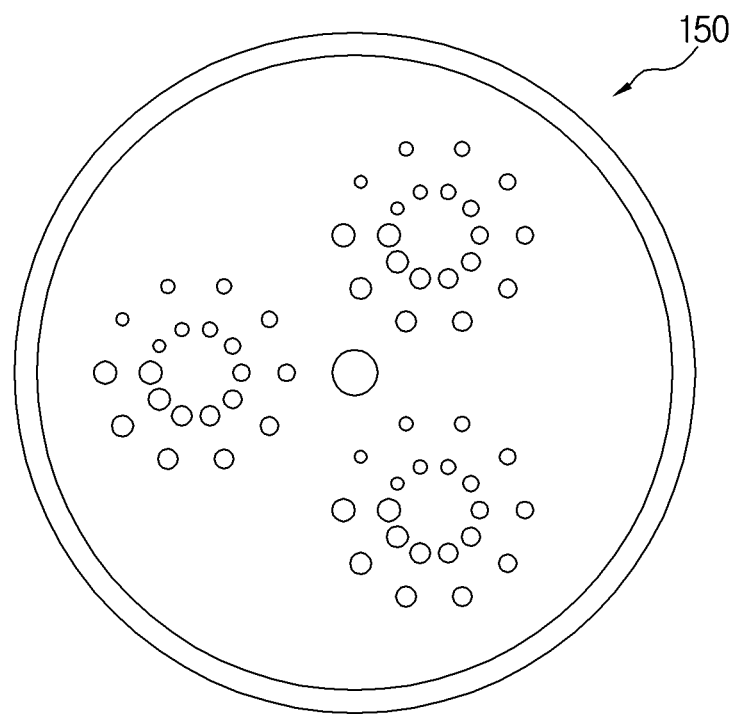

In addition, FIG. 9 is a perspective view and a flat sectional view showing a contrast resolution evaluation apparatus of an ultra high field multi-purpose performance evaluation phantom 100 for small animals according to the present invention.

Figure 10:
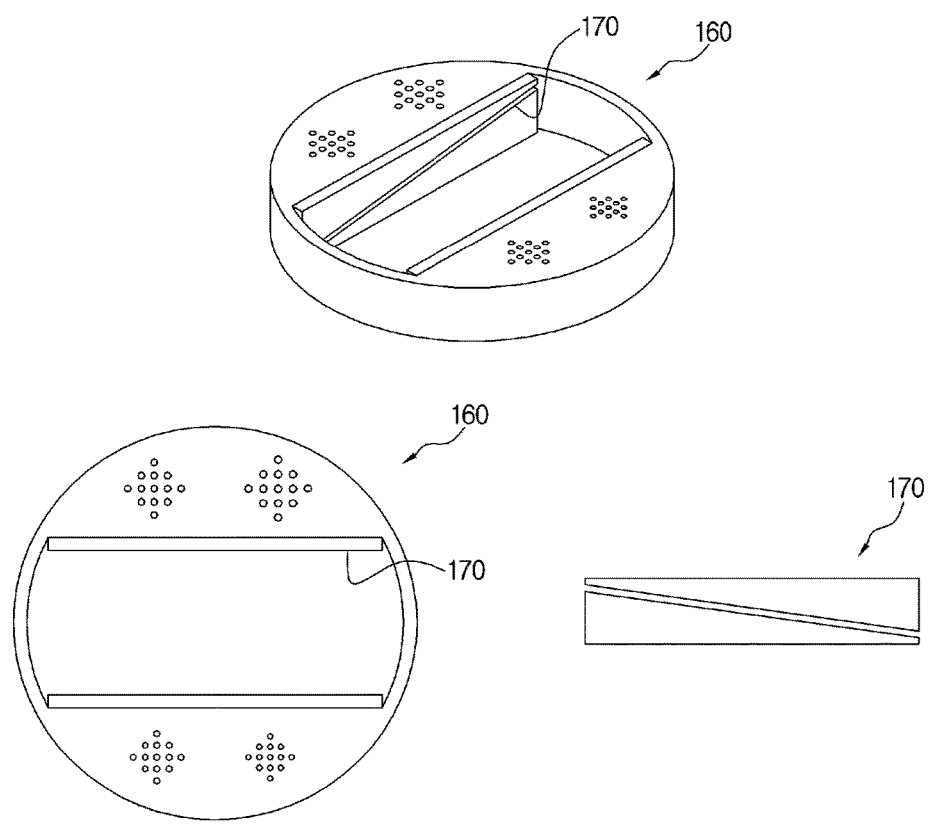
FIG. 10 is a perspective view and a flat sectional view showing a spatial resolution evaluation apparatus and a slice thickness evaluation apparatus of a phantom according to the present invention, which can be simultaneously acquired, and a longitudinal sectional view showing components thereof.

In addition, FIG. 10 is a perspective view and a flat sectional view showing a spatial resolution evaluation apparatus and a slice thickness evaluation apparatus 170 of a phantom 100 for small animals according to the present invention, which can be simultaneously acquired, and a longitudinal sectional view showing components thereof.

Figure 11:
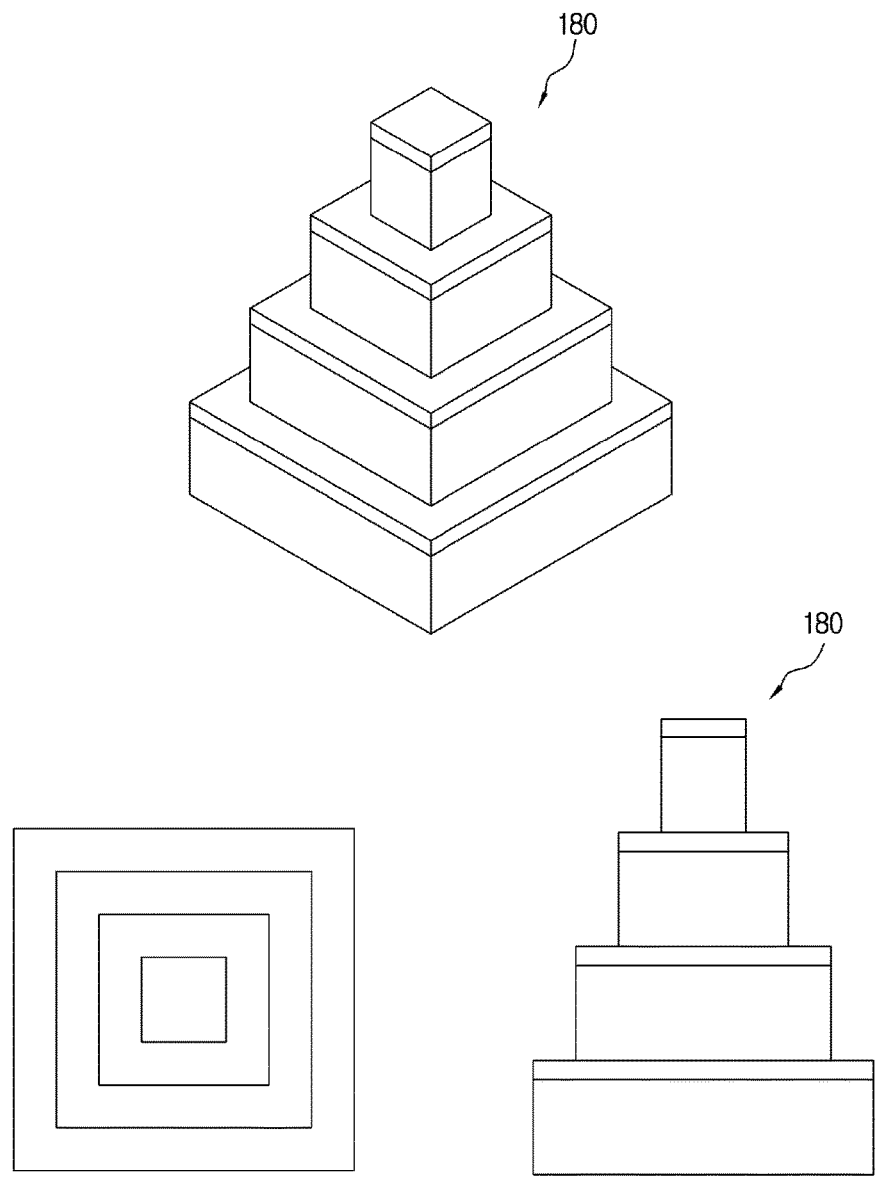
FIG. 11 is a perspective view, a flat sectional view and a longitudinal sectional view showing a specific example of an apparatus for analyzing brain metabolites and evaluating quality control of MRS at a lower end portion of a phantom according to the present invention.

In addition, FIG. 11 is a perspective view, a flat sectional view and a longitudinal sectional view showing a specific example of an apparatus for analyzing brain metabolites and evaluating quality control of MRS 180 at a lower end portion of a phantom 100 for small animals according to the present invention.

As shown in FIGS. 2 and 3, a multi-purpose phantom 100 for evaluating performance of an ultra high field animal MRI apparatus according to the present invention is configured of an outer container 110, an upper stopper portion 112, and a lower stopper portion 114.

In addition, four inner containers 120 are configured at the upper end portion, and one inner container 120 formed as a layer is configured at the lower end portion.

A three-dimensional geometric accuracy evaluation apparatus 130, a slice position accuracy evaluation apparatus, a contrast resolution evaluation apparatus 150 and a spatial resolution and slice thickness evaluation apparatus are basically configured inside the outer container 110 of the phantom 100 according to the present invention.

The upper stopper portion 112 of the outer container 110 has a thickness of 5 mm and a diameter of 60 mm, and the center portion of the upper stopper portion 112 is formed of a hole having a thickness of 5 mm and a diameter of 16 mm for the polyethylene bolt portion of the upper injection hole to configure the phantom 100 of the present invention in an integration form.

The upper stopper portion 112 is not magnetized even in a strong magnetic field since it is configured of an acrylic material.

Four insertion holes at the upper end portion eliminate a cause of artifacts created due to air and prevent inflow of the air by inserting a rubber ring around the lower end portion of the bolt of the upper stopper.

The outer container 110 is configured of a cylindrical acrylic material having a thickness of 5 mm, a diameter of 60 mm, and since the outer container 110 is configured of an acrylic material, it is not magnetized even in a strong magnetic field.

Injection holes having an outer diameter of 14 mm and an inner diameter of 12 mm are formed at a predetermined distance from the center of the outer container 110 at 15 mm intervals of center distance to inject a solution changing the liver metabolite and lipid contents and may be arranged while keeping a distance to reduce artifacts or the like with respect to the air of each inner container 120.

Each inner container 120 at the upper end portion 112 is inserted into the insertion hole formed on the top surface of the outer container 110 and closed using a stopper, and thus the four inner containers 120 are installed on the top surface of the outer container 110.

As shown in FIG. 5, the inner container 120 is a container having a top portion measuring 5 mm in thickness, 14 mm in outer diameter, 12 mm in inner diameter and 21 mm in height. The inner container 120 may compare images based on difference of concentration by acquiring T1 and T2 relaxography from MRI and measure quantity accuracy and position accuracy of a volume of interest (VOI) by acquiring amounts of materials and metabolites contained in a voxel using a single voxel technique of magnetic resonance spectroscopy.

A partial volume effect can be prevented by accurately selecting a volume of interest by using a thin acrylic material in the four containers like this.

In addition, since the inner container 120 is also configured of an acrylic material, it is not magnetized even in a strong magnetic field.

In the area other than the inner containers 120 installed at the upper and lower end portions inside the outer container 110, a component for performing quality control of MRI is rearranged and inserted in a predetermined position to minimize an empty space.

That is, a frame of the three-dimensional geometric accuracy evaluation apparatus 130 for evaluating three-dimensional geometric accuracy is installed at the upper end portion inside the outer container 110, and the slice position accuracy evaluation apparatus and the contrast resolution evaluation apparatus 150 are installed under the three-dimensional geometric accuracy evaluation apparatus 130 in order, and the spatial resolution evaluation apparatus and the slice thickness evaluation apparatus 170 are installed to face each other at the same height to embody them simultaneously.

The three-dimensional geometric accuracy evaluation apparatus 130 is arranged at the upper end portion of the outer container 110 as shown in FIG. 6, and a frame of lattice is formed in three directions of x, y and z axes.

All the three directions are used for geometric accuracy evaluation, and the apparatus is manufactured to have a diameter of 56 mm and a thickness of 4 mm and configured as a frame of a lattice shape.

The frame of a lattice shape has a feature of a rectangle of 4 mm wide, 4 mm long and 4 mm high and is configured of one hundred and twenty lattices in total.

The innermost frame is 2 mm away from the center, and the frames are located 1 mm away from each other.

Such a three-dimensional geometric accuracy evaluation apparatus 130 may determine an accurate length of an MRI image on the x, y and z axes and evaluate position accuracy within a permitted and limited error range by calculating a distance of a measurement target in the image as a position, an intersection and a distance between intersections of each lattice when the MRI image is acquired.

As shown in FIG. 6 of the three-dimensional geometric accuracy evaluation apparatus 130, a pillar for prior position selection and accuracy selection is inserted.

A focal point of the MRI may be minutely and precisely selected, and this is an apparatus and a part needed most for three-dimensional geometric accuracy evaluation.

The pillar is 9 mm long and 1 mm thick and is configured in three directions of x, y and z axes from an overlapped point. The lower end portion of the three-dimensional geometric accuracy evaluation apparatus 130 is installed in four directions in total, and precise and intensified three-dimensional geometric accuracy evaluation and quality control may be accomplished.

A supporting body 135 is installed at the lower end portion of the three-dimensional geometric accuracy evaluation apparatus 130 inside the outer container 110 as shown in FIG. 7.

The portions protruded toward inside the outer container 110 are 2 mm in width, 4 mm in length and 26 mm in height. The upper end portion of the supporting body supports the three-dimensional geometric accuracy evaluation apparatus 130, and the lower end portion is combined with a slice position evaluation apparatus 140.

The slice position evaluation apparatus 140 is installed at a position appropriate for installing the supporting body and capable of enhancing space utilization and durability.

The slice position evaluation apparatus 140 combined with the supporting body inside the outer container 110 is shown in FIG. 8.

The internal component combines apparatuses of a stair form and a linear form and evaluates precise slice positions of four steps in total.

The slice position evaluation apparatus 140 is installed to perform performance evaluation by measuring a slice position based on the intersection of the upper portion and the lower portion of the stair form apparatus within an error and limit range, and it is fixed in the shape of a cross to support apparatuses if the stair form and the linear form and enhance durability.

Height of the layers of the stair form apparatus is 8 mm, 6 mm, 4 mm and 2 mm clockwise, and the linear form apparatus is configured to selectively measure thickness of various slices by measuring total height in four steps of 24 mm, 18 mm, 12 mm and 6 mm.

As shown in FIG. 9, the contrast resolution evaluation apparatus 150 for evaluating contrast resolution is positioned at the center portion inside the outer container 110 and is installed in the form of arranging three disks in layers supported by the central supporting body.

Contrast evaluation holes are positioned at zero, one hundred and twenty and two hundred and forty degrees from a point 14 mm away from the center of the disk, rotate thirty six degrees at a time along clockwise circular paths formed in the middle and circumferential portions centering on a point apart from the other centers, and are formed in bundles at regular intervals to have diameters gradually increasing in order of 1 mm, 1.1 mm, 1.2 mm, 1.3 mm, 1.4 mm, 1.5 mm, 1.6 mm, 1.7 mm, 1.8 mm and 1.9 mm, and two contrast evaluation holes starting first toward the end of the arc of each bundle are formed in parallel at the same length intervals of 4 mm.

The contrast resolution evaluation apparatus 150 is formed as three layers to be optimally used inside the ultra high field animal MRI apparatus, and the disks are 0.075 mm, 0.05 mm and 0.1 mm in thickness and arranged toward the bottom.

When an MRI image is acquired, acquisition of images of each slice is used to evaluate performance of the apparatus after the number of distinguishable holes in the layer of each thickness is measured by grasping by with eyes.

An apparatus capable of measuring accuracy of spatial resolution and slice thickness of the lower end portion of the contrast resolution evaluation apparatus 150 is arranged.

As shown in FIG. 10, a space is formed at the center portion, and then a slice thickness evaluation apparatus is arranged at the inner portion, and, at the same time, the spatial resolution evaluation apparatus 160 is arranged at the outer portion, with respect to the center portion.

The spatial resolution evaluation apparatus 160 is arranged after being divided into four portions and configured of ultra high field custom-tailored diameters of 1 mm, 0.9 mm, 0.8 mm and 0.7 mm and a thickness of 10 mm, and they are respectively arranged after selecting an appropriate position (a position apart as far as the diameter of the hole) in order to minimize interference between the space evaluation holes.

The bundles of the space evaluation holes are arranged in a diamond shape, and thirteen space evaluation holes are configured in a bundle.

The evaluation apparatus like this is used to analyze whether or not the spatial resolution can be clearly classified and distinguished through an image or existence of artifacts when an MRI image is acquired by the space evaluation holes in each bundle of space evaluation holes.

Accordingly, through the evaluation of the spatial resolution evaluation apparatus 160 in each step, evaluation is extended to a portion which is not evaluated and verified so that the evaluation may be accomplished further accurately and easily.

In addition, evaluation errors are minimized by placing a predetermined distance.

The slice thickness evaluation apparatus 170 arranged inside the spatial resolution evaluation apparatus 160 is configured to be integrated with the spatial resolution evaluation apparatus 160, may be simultaneously acquired when an MRI image is acquired and is arranged at the same position to maximize efficiency of time.

In addition, the slice thickness evaluation apparatus 170 is configured in a precise and minute stair form and is simultaneously designed at the upper portion and the lower portion 2 mm inside in width in the form of a stair of 0.005 mm for an ultra high field quality control standard.

In addition, the left and right widths are obliquely sloped downward and positioned in a direction opposite to each other.

The slice thickness measurement device is 50 mm wide and 2 mm long and is configured in the form of a stair sloped downward with 1 mm width. The apparatus may perform accurate evaluation at a time of measurement compared with an existing apparatus of a linear form, and it is a custom-tailored ultra high field animal apparatus which may perform evaluation at a minimum thickness in the apparatus.

FIG. 11 is a view showing the inner container 180 for performing quality control of MRS according to the present invention. The inner container 180 is positioned at a lower portion of the outer container 110 and forms an insertion hole having a diameter of 6 mm to inject a solution mimicking a brain metabolite. In addition, insertion holes are formed at positions 23.5 mm away from each other at both sides to inject a solution other than the brain metabolite into the outer container 110. The insertion holes are used to fill in the portions other than the inner container 120 of a layered shape and the four cylindrical inner containers 120 at the upper portion, and the other portions are filled with copper sulfate ($CuSO_4$; 0.7 g/L) injected through the insertion holes. Like this, the diluted copper sulfate solution performs a function of reducing T1 relaxation time of water to intensify a signal and show a result of short time efficiency when MRI and MRS are acquired.

The inner container 180 of FIG. 11 is formed in a shape of the same dimension in width and length of 32 mm, 23 mm, 14 mm and 5 mm inside the container from the bottom to the top, and it is a container of stepped layers decreasing in order of following layers.

In addition, it is formed as rectangular parallelepiped layers measuring 10 mm in height. Owing to the shape of the inner container 180, components of metabolites can be analyzed and concentration, quantity accuracy and position accuracy can be measured by changing amounts of the metabolites and types of the materials contained in a voxel in each stepped layer.

Since the inner container 180 is configured as a rectangular parallelepiped form rather than a conventional cylindrical form, it is easy and accurate to designate a position of a voxel, and artifacts with respect to the acrylic effect can be reduce to the minimum when a voxel is designated.

The shape of the inner container 180 like this may prevent a partial volume effect owing to position accuracy in selecting a volume of interest and, in addition, may present a method of enhancing accuracy owing to the property of not being magnetized even in a strong magnetic field and practically improve a result of standard quality control.

Solutions similar to the brain metabolites are filled in the stepped layers inside the inner container 120 of FIG. 11 to express the brain metabolites, and Monopotassium phosphate (KH2PO4; 32 mM) is mixed with Tripotassium phosphate (K3PO4; 18 mM) to make pH7 similar to the components of a human body. In addition, metabolites mentioned below are added to the solution in order to mimic the brain metabolites (N-acetyl-Laspartic acid; NAA; 12.5 mM, Creatine hydrate; Cr; 10.0 mM, Choline chloride; Cho; 3.0 mM, Myo-inositol; mI; 7.5 mM, L-Glutamic acid; Glu; 12.5 mM, DL-lactic acid; Lac; 5.0 mM, 4-Aminobutyric acid; GABA; 10.0 mM, L-Alanine; Al; 10.0 mM, L-Glutamine; Gln; 12.5 mM, Taurine; Tau; 6.0 mM).

A voxel size artifact test, a signal-to-noise ratio, a chemical movement, a line width, a water suppression percent, symmetry of water signal, accuracy of volume position, and accuracy of volume quantity are analyzed by using the inner container 180 for MRS quality control at the lower end portion.

The outer container 110 is configured by placing a space having a thickness of 5 mm at the center portion of the outer container 110 as shown in FIGS. 2, 3 and 4 so that image signal intensity uniformity and percent signal ghosting may be evaluated when MRI is evaluated.

A custom-tailored phantom 100 is invented inside an animal MRI apparatus by arranging such evaluation apparatuses and maximizing efficiency of the evaluation apparatuses.

According to the multi-purpose phantom 100 for evaluating performance of an ultra high field animal MRI apparatus of the present invention described above, concentration of a brain metabolite and a liver metabolite can be changed.

In addition, starting from an inner container 120 for adding a liver metabolite and a lipid and an apparatus for evaluating precise three-dimensional geometric accuracy, the present invention proposes measurement of distinguishable slice positions of four steps, a spatial resolution evaluation apparatus 160 formed in three layers, an apparatus 150 for evaluating slice thickness and contrast resolution which can be simultaneously acquired, and an inner container 180 of a stair form for injecting a solution mimicking a brain metabolite.

In addition, the inner container 120 and the evaluation apparatuses propose an arrangement for minimizing the space and miniaturizing volume of the phantom 100 and propose a volume, a thickness and a length optimized to a coil for animals (a rate or mouse body coil) inside the animal MRI apparatus.

In addition, the phantom 100 of the present may provide an effect of reducing artifacts, providing preciseness and enhancing temporal efficiency by minimizing a space with respect to the coil.

In addition, the inner container 120 formed at the upper end portion of the outer container 110 to add a liver metabolite and a lipid may change components of the lipid (fatty-acid, %) and add the components into four inner containers 120 and may provide an effect of further precisely and accurately perform contrast evaluation by manufacturing an acrylic disk for evaluating contrast resolution at the center of the outer container 110 in an ultra high field custom-tailored thickness and separating the disk into three layers of 0.050 mm, 0.075 mm and 0.100 mm.

In addition, an inner container 180 formed as rectangular parallelepiped layers which can optimize the size and position of a voxel while focusing on single voxel spectroscopy is inserted, and this may provide an effect of minimizing influence of artifacts or removing the artifacts.

In addition, the inner container 180 proposed in the present invention is positioned at the lowest end portion and may adjust amounts of brain metabolites, implement a desired signal when a spectrum is acquired by using MRS, and provide an effect of performing accurate quantitative evaluation of concentration.

In conclusion, a multi-purpose performance evaluation method and apparatus in an ultra high field animal magnetic resonance imaging system according to the present invention may (1) measure quality control for evaluating an accumulated amount of a lipid of a liver metabolite, three-dimensional geometric accuracy of an MRI image, intensified spatial resolution, contrast resolution, accuracy of slice position of four steps, image intensity uniformity, signal percent, slice thickness and the like, (2) quantitatively evaluate and analyze brain metabolites while a signal-to noise ratio, accuracy of volume position, accuracy of volume quantity, symmetry of water signal, a water suppression percent, a chemical movement, a line width and the like are measured more accurately than using the conventional phantom 100 by selecting an accurate voxel position when a spectrum is acquired by using the MRS, (3) provide an effect of acquiring quality control using a micro phantom 100, including simultaneous acquisition, in a short time by simultaneously acquiring the evaluation and analysis functions described above, together with maintaining performance of equipment and minimizing artifacts, when MRI and MRS of an MRI system and changes of metabolites are evaluated, and (4) provide an effect of improving reliability of equipment performance.

According to the multi-purpose phantom for evaluating performance of an ultra high field animal MRI apparatus proposed by the present invention, concentration of a brain metabolite and a liver metabolite can be changed.

In addition, starting from an inner container 120 for adding a liver metabolite and a lipid and an apparatus for evaluating precise three-dimensional geometric accuracy, the present invention proposes measurement of distinguishable slice positions of four steps, a spatial resolution evaluation apparatus 160 formed as three layers, an apparatus 150 for evaluating slice thickness and contrast resolution which can be simultaneously acquired, and an inner container 180 of a stair form for injecting a solution mimicking a brain metabolite.

In addition, the inner container 180 and the evaluation apparatuses propose an arrangement for minimizing the space and miniaturizing volume of the phantom and propose a volume, a thickness and a length optimized to a coil for animals (a rate or mouse body coil) inside the animal MRI apparatus.

In addition, the phantom of the present may provide an effect of reducing artifacts, providing preciseness and enhancing temporal efficiency by minimizing a space with respect to the coil.

In addition, In addition, the inner container 120 formed at the upper end portion of the outer container to add a liver metabolite and a lipid may change components of the lipid (fatty-acid, %) and add the components into four inner containers and may provide an effect of further precisely and accurately perform contrast evaluation by manufacturing an acrylic disk for evaluating contrast resolution at the center of the outer container in an ultra high field custom-tailored thickness and separating the disk into three layers of 0.050 mm, 0.075 mm and 0.100 mm.

In addition, an inner container 180 formed as rectangular parallelepiped layers which can optimize the size and position of a voxel while focusing on single voxel spectroscopy is inserted, and this may provide an effect of minimizing influence of artifacts or removing the artifacts.

In addition, the inner container 180 proposed in the present invention is positioned at the lowest end portion and may adjust amounts of brain metabolites, implement a desired signal when a spectrum is acquired by using MRS, and provide an effect of performing accurate quantitative evaluation of concentration.

In conclusion, a multi-purpose performance evaluation method and apparatus in an ultra high field animal magnetic resonance imaging system according to the present invention may (1) measure quality control for evaluating an accumulated amount of a lipid of a liver metabolite, three-dimensional geometric accuracy of an MRI image, intensified spatial resolution, contrast resolution, accuracy of slice position of four steps, image intensity uniformity, signal percent, slice thickness and the like, (2) quantitatively evaluate and analyze brain metabolites while a signal-to-noise ratio, accuracy of volume position, accuracy of volume quantity, symmetry of water signal, a water suppression percent, a chemical movement, a line width and the like are measured more accurately than using the conventional phantom 100 by selecting an accurate voxel position when a spectrum is acquired by using the MRS, (3) provide an effect of acquiring quality control using a micro phantom 100, including simultaneous acquisition, in a short time by simultaneously acquiring the evaluation and analysis functions described above, together with maintaining performance of equipment and minimizing artifacts, when MRI and MRS of an MRI system and changes of metabolites are evaluated, and (4) provide an effect of improving reliability of equipment performance.

The effects which can be obtained in the present invention are not limited to the effects mentioned above, and unmentioned other effects may be clearly understood by those skilled in the art from the following descriptions.

As mentioned in the foregoing description, the detailed descriptions for the preferred embodiments of the present invention are provided to be implemented by those skilled in the art. While the present invention has been described and illustrated herein with reference to the preferred embodiments thereof, it will be apparent to those skilled in the art that various modifications and variations can be made therein without departing from the spirit and scope of the invention. Thus, it is intended that the present invention covers the modifications and variations of this invention that come within the scope of the appended claims and their equivalents. For instance, the respective configurations disclosed in the aforesaid embodiments of the present invention can be used by those skilled in the art in a manner of being combined with one another. Therefore, the present invention is non-limited by the embodiments disclosed herein but intends to give a broadest scope matching the principles and new features disclosed herein.

The present invention may be embodied in other specific forms without departing from the spirit and essential characteristics of the present invention. Therefore, the detailed description is to be construed as limited to be considered in all respects illustrative devised. The scope of the invention should be determined by reasonable interpretation of the appended claims, and all modifications within equivalent ranges of the present invention are included in the scope of the present invention. In addition, the combination does not have an explicit cited relation of claims claims to constitute the embodiment or may include new claims by amendment after application.

What is claimed is:

1. A phantom for evaluating performance of an ultra high field Magnetic Resonance Imaging (MRI) apparatus, the phantom comprising:
    an outer container opened and closed using a stopper and formed with an insertion hole for injecting components of a liver metabolite and a lipid;
    an inner container for quantitatively evaluating the components of the liver metabolite and the lipid, acquiring an MRI image using a spin echo sequence, and acquiring a relaxation time through spectroscopy using a single voxel technique of the MRI apparatus;
    a geometric accuracy evaluation apparatus installed at an upper end portion of the outer container in a shape of three-dimensional lattice type frame;
    slice position evaluation apparatuses of different shapes, capable of measuring a position of a slice in a middle of the outer container;
    a contrast resolution evaluation apparatus configured of a plurality of holes in the middle of the outer container to perform evaluation at regular intervals;
    a spatial resolution evaluation apparatus installed inside the outer container and having a plurality of hole bundles configured of space evaluation holes, wherein the space evaluation holes are formed and arranged to have different diameters;
    a slice thickness evaluation apparatus installed at a height that is equal to a height of the spatial resolution evaluation apparatus and attached to the outer container to be formed in a shape of a stair; and
    a brain metabolite evaluation apparatus configured of a plurality of layers at a lower portion of the outer container.

2. The phantom according to claim 1, wherein the phantom for evaluating performance of an ultra high field Magnetic Resonance Imaging (MRI) apparatus is used for small animals.

3. The phantom according to claim 1, wherein the outer container further includes an injection hole, in which holes uniformly distributed from a center portion of a top surface are opened and closed using a plurality of stoppers.

4. The phantom according to claim 1, wherein the inner container acquires T1 and T2 relaxation images by using a spin echo sequence of a method of acquiring a main image of the MRI image, acquires T1 and T2 relaxation images related to the inner container through spectroscopy using the single voxel technique of the MRI apparatus, and compares the acquired T1 and T2 relaxation images and the acquired T1 and T2 relaxation spectra with each other.

5. The phantom according to claim 1, wherein the slice position evaluation apparatus measures four step slice positions of a cross shape in the middle of the outer container.

6. The phantom according to claim 1, wherein the plurality of holes of the contrast resolution evaluation apparatus is formed in a circular shape and arranged regularly.

7. The phantom according to claim 1, wherein the plurality of layers of the brain metabolite evaluation apparatus is configured of four layers.

8. The phantom according to claim 1, wherein the inner container includes:
- a stopper formed of a polyethylene bolt capable of simultaneously injecting air and preventing leakage of water through a plurality of holes; and
- a rubber ring inserted around a lower end portion of the stopper.

9. The phantom according to claim 1, wherein the inner container contains an injected solution mimicking the liver metabolite.

10. The phantom according to claim 9, wherein the inner container contains an injected solution mimicking the lipid.

11. The phantom according to claim 1, wherein each lattice frame of the shape of three-dimensional lattice type frame is regularly configured of same lattices and used for analysis on x, y and z axes.

12. The phantom according to claim 1, wherein a pillar frame functioning as a supporting body of the geometric accuracy evaluation apparatus is additionally inserted.

13. The phantom according to claim 1, wherein the slice position evaluation apparatus is configured of three layers, and height of the three layers decreases at regular intervals counterclockwise.

14. The phantom according to claim 1, wherein the space evaluation holes of a regular array are arranged in bundles at three positions on each disk of the contrast resolution evaluation apparatus.

15. The phantom according to claim 1, wherein the hole bundles of the spatial resolution evaluation apparatus are formed by arranging a plurality of space evaluation holes of a same diameter at a predetermined position and grouping the space evaluation holes in a diamond shape.

16. The phantom according to claim 1, wherein the slice thickness evaluation apparatus is a structure of a same width, formed in a shape obliquely sloping down toward left and right.

17. The phantom according to claim 1, wherein a spatial resolution evaluation and a slice thickness evaluation are simultaneously performed using one slice since the spatial resolution evaluation apparatus and the slice thickness evaluation apparatus are arranged in a row.

18. The phantom according to claim 1, further comprising a second inner container configured of layers of rectangular parallelepiped steps having inner diameters gradually increasing from a top to a bottom.

19. The phantom according to claim 18, wherein a solution mimicking a brain metabolite is injected into the stepped layers from an upper end portion of the second inner container.

20. The phantom according to claim 1, wherein a copper sulfate solution and a sodium chloride aqueous solution are injected into a second inner container through two injection holes.

21. The phantom according to claim 1, wherein the outer container, the inner container, the geometric accuracy evaluation apparatus, the slice position evaluation apparatus, the contrast resolution evaluation apparatus, the spatial resolution evaluation apparatus, the slice thickness evaluation apparatus and the brain metabolite evaluation apparatus are configured of an acrylic material.

* * * * *